United States Patent [19]

Santini, Jr. et al.

[11] Patent Number: 5,797,898

[45] Date of Patent: Aug. 25, 1998

[54] MICROCHIP DRUG DELIVERY DEVICES

[75] Inventors: John T. Santini, Jr., Jackson, Mich.; Michael J. Cima, Lexington; Robert S. Langer, Newton, both of Mass.

[73] Assignee: Massachusetts Institute of Technology, Cambridge, Mass.

[21] Appl. No.: 675,375

[22] Filed: Jul. 2, 1996

[51] Int. Cl.$^6$ .................................................. A61K 9/22
[52] U.S. Cl. .......................................... 604/890.1; 604/93
[58] Field of Search ........................... 604/890.1, 891.1, 604/93; 128/899

[56] References Cited

U.S. PATENT DOCUMENTS

| | | | |
|---|---|---|---|
| 3,692,027 | 9/1972 | Ellinwood | 128/260 |
| 4,003,379 | 1/1977 | Ellinwood | 128/260 |
| 4,146,029 | 3/1979 | Ellinwood | 128/260 |
| 4,360,019 | 11/1982 | Jassawalla | 128/213 R |
| 4,507,115 | 3/1985 | Kambara et al. | 604/135 |
| 4,585,652 | 4/1986 | Miller et al. | 424/83 |
| 4,731,051 | 3/1988 | Fischell | 604/67 |
| 4,793,825 | 12/1988 | Benjamin et al. | 604/891 |
| 4,994,023 | 2/1991 | Wellinghoff et al. | 604/20 |
| 5,041,107 | 8/1991 | Heil, Jr. | 604/891.1 |
| 5,167,625 | 12/1992 | Jacobsen et al. | 604/890.1 |
| 5,170,801 | 12/1992 | Casper et al. | 128/769 |
| 5,196,002 | 3/1993 | Hanover et al. | 604/891.1 |
| 5,254,081 | 10/1993 | Maurer et al. | 604/20 |
| 5,279,607 | 1/1994 | Schentag et al. | 604/890 |
| 5,318,557 | 6/1994 | Gross | 604/891.1 |
| 5,336,213 | 8/1994 | D'Angelo et al. | 604/890.1 |
| 5,368,588 | 11/1994 | Bettinger | 604/891.1 |

(List continued on next page.)

OTHER PUBLICATIONS

Rae, et al., "Pulsatile Drug Release By Electric Stimulus", *ACS Symposium Series*, 545:98–110 (1994).

Bates, et al., "New Amorphous Thin-Film Lithium Electrolyte And Rechargeable Microbattery" *IEEE 35th International Power Sources Symposium*, 337–339 (1992).

Jaeger, Ed., "Introduction To Microelectronic Fabrication", vol. V, Modular Series On Solid State Devices, Addison-Wesley, Reading, MA, 1988.

Jones & Akridge, "Development And Performance Of A Rechargeable Thin-Film Solid-State Microbattery", *J. Power Sources*, 54:63–67 (1995).

Kwon, et al., "Electrically Erodible Polymer Gel For Controlled Release Of Drugs", *Nature*, 354:291–293 (1991).

(List continued on next page.)

*Primary Examiner*—Mark Bockelman
*Assistant Examiner*—Ellen Tao
*Attorney, Agent, or Firm*—Arnall Golden & Gregory, LLP

[57] ABSTRACT

Microchips are provided, which control both the rate and time of release of multiple chemical substances and which allow for the release of a wide variety of molecules in either a continuous or pulsatile manner. In all of the preferred embodiments, a material that is impermeable to the drugs or other molecules to be delivered and the surrounding fluids is used as the substrate. Reservoirs are etched into the substrate using either chemical (wet) etching or ion beam (dry) etching techniques well known in the field of microfabrication. Hundreds to thousands of reservoirs can be fabricated on a single microchip using these techniques. The molecules to be delivered are inserted into the reservoirs by injection or spin coating methods in their pure form or in a release system. Exemplary release systems include polymers and polymeric matrices, non-polymeric matrices, and other excipients or diluents. The physical properties of the release system control the rate of release of the molecules. The reservoirs can contain multiple drugs or other molecules in variable dosages. The filled reservoirs can be capped with materials that either degrade or allow the molecules to diffuse passively out of the reservoir over time or materials that oxidize and dissolve upon application of an electric potential. Release from an active device can be controlled by a preprogrammed microprocessor, remote control, or by biosensors.

29 Claims, 7 Drawing Sheets

U.S. PATENT DOCUMENTS

| | | | |
|---|---|---|---|
| 5,368,704 | 11/1994 | Madou et al. | 204/129.55 |
| 5,387,419 | 2/1995 | Levy et al. | 424/422 |
| 5,443,508 | 8/1995 | Giampapa | 604/891.1 |
| 5,490,962 | 2/1996 | Cima et al. | 264/22 |
| 5,518,680 | 5/1996 | Cima et al. | 264/401 |

OTHER PUBLICATIONS

Tierney and Martin, "Electroreleasing Composite Membranes For Delivery Of Insulin And Other Biomacromoleculers", *J. Electrochem. Soc.*, 137(6):2005–2006 (1990).

Tierney and Martin, "New Electrorelease Systems Based On Microporous Membranes", *J. Electrochem. Soc.*, 137(12):3789–3793 (1990).

Uhrich, et al., "Synthesis And Characterization Of Degradable Poly(anhydride–co–imides)", *Macromolecules*, 28:2184–2193 (1995).

Wolf & Tauber, "Silicon Processing For The VLSI Era", vol. 1—Process Technology, Lattice Press, Sunset Beach, CA 1986.

MICROCHIP 10

| | RELEASE SYSTEM CONTAINING THE DRUG OR OTHER MOLECULE |
|---|---|
| | RESERVOIR CAP MATERIAL |
| | INSULATOR/ETCH MASK MATERIAL |

 DEGRADABLE RESERVOIR CAP MATERIAL
 NON-DEGRADABLE RESERVOIR-CAP MATERIAL
 DEGRADABLE RELEASE SYSTEM
 NON-DEGRADABLE RELEASE SYSTEM
 PURE DRUG OR OTHER MOLECULE (SOLID, LIQUID, OR GEL FORM)
 INSULATOR/ETCH MASK MATERIAL

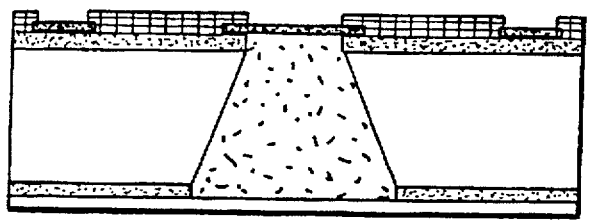
FIG. 7a
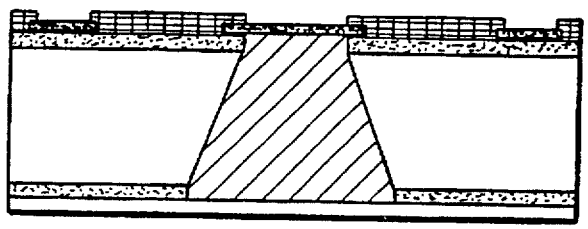
FIG. 7b
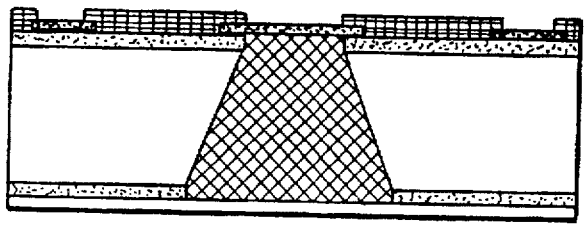
FIG. 7c
 INSULATOR / ETCH MASK MATERIAL
 ANODE AND CATHODE MATERIAL
 INSULATOR OVERLAYER
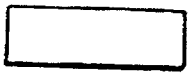 DEGRADABLE RELEASE SYSTEM
 NON-DEGRADABLE RELEASE SYSTEM
 PURE DRUG OR OTHER MOLECULE (SOLID, LIQUID, OR GEL FORM)

5,797,898

MICROCHIP DRUG DELIVERY DEVICES

BACKGROUND OF THE INVENTION

This invention relates to miniaturized drug delivery devices and more particularly, to controlled time and rate release multi-welled drug delivery devices.

Drug delivery is an important aspect of medical treatment. The efficacy of many drugs is directly related to the way in which they are administered. Some therapies require that the drug be repeatedly administered to the patient over a long period of time. This makes the selection of a proper drug delivery method problematic. Patients often forget, are unwilling, or are unable to take their medication. Drug delivery also becomes problematic when the drugs are too potent for systemic delivery. Therefore, attempts have been made to design and fabricate a delivery device which is capable of the controlled, pulsatile or continuous release of a wide variety of molecules including, but not limited to, drugs and other therapeutics.

Controlled release polymeric devices have been designed to provide drug release over a period of time via diffusion of the drug out of the polymer and/or degradation of the polymer over the desired time period following administration to the patient. However, these devices are relatively simple.

U.S. Pat. No. 5,490,962 to Cima, et al. discloses the use of three dimensional printing methods to make more complex devices which provide release over a desired time frame, of one or more drugs. Although the general procedure for making a complex device is described, specific designs are not detailed.

U.S. Pat. No. 4,003,379 to Ellinwood describes an implantable electromechanically driven device that includes a flexible retractable walled container, which receives medication from a storage area via an inlet and then dispenses the medication into the body via an outlet. U.S. Pat. No. 4,146,029 and U.S. Pat. No. 3,692,027 to Ellinwood disclose self-powered medication systems that have programmable miniaturized dispensing means. U.S. Pat. No. 4,360,019 to Jassawalla discloses an implantable infusion device that includes an actuating means for delivery of the drug through a catheter. The actuating means includes a solenoid driven miniature pump. All of these devices include miniature power-driven mechanical parts that are required to operate in the body, i.e., they must retract, dispense, or pump. These are complicated and subject to breakdown. Moreover, due to complexity and size restrictions, they are unsuitable to deliver more than a few drugs or drug mixtures at a time.

It is therefore an object of the present invention to provide a simple to use and manufacture, dependable, multi-welled delivery device for drugs and other molecules which can operate for weeks or years at a time.

It is another object of the present invention to provide such a device that allows delivery of drugs or other molecules in either a pulsatile or continuous manner.

It is yet another object of the present invention to provide such a device that allows the delivery to be controlled either passively or actively.

It is also an object of the present invention to provide such a device that can hold many different drugs or other molecules of varying dosages and is small enough to be implantable, if desired.

SUMMARY OF THE INVENTION

Microchips for delivery of a wide variety of molecules are provided. Microchips are miniaturized devices constructed using methods commonly applied to the manufacture of integrated circuits such as ultraviolet (UV) photolithography, reactive ion etching, and electron beam evaporation. The microchips provide control over the rate the molecules are released as well as the time at which release begins. The time of release can be controlled passively or actively.

In the preferred embodiments, a material which is impermeable to the surrounding fluids and to the molecules to be delivered is used as the substrate. Examples of substrate materials include ceramics, semiconductors such as silicon, and degradable and non-degradable polymers. Reservoirs are etched into the substrate using either chemical (wet) etching or ion (dry) etching techniques commonly used in microfabrication. Hundreds to thousands of reservoirs can be created in this manner and contained in a single microchip. Typically, a release system containing the molecule to be delivered is inserted into the reservoirs by injection or other means. When present, the release system controls the rate of release of the molecule. The rate of release is a function of the composition and structure of the release system. However, the device design makes it possible to fill the reservoirs with pure molecules (no release system) in solid or liquid form. Each of the reservoirs of a single microchip can contain different molecules and/or different amounts, which can be released independently.

In a preferred embodiment, the reservoir cap enables passive timed release, not requiring a power source, of molecules. The reservoirs are capped with materials that degrade at a known rate or have a known permeability (diffusion constant) for the molecules to be delivered. Therefore, the degradation or diffusion characteristics of the cap material determine the time at which the release of molecules in a particular reservoir begins. In effect, the microchip provides dual control of the release of molecules by selection of the release system (rate controller) and selection of the cap material (time controller, and in some cases, rate controller).

In another preferred embodiment, the reservoir cap enables active timed release, requiring a power source, of molecules. In this embodiment, the reservoir caps consist of a thin film of conductive material that is deposited over the reservoir and patterned into the shape of an anode surrounded by a cathode. Conductive materials capable of dissolving into solution upon the application of an electric potential, including metals such as copper, gold, silver, and zinc and some polymers, are used in the active timed release device. When an electric potential is applied across the electrodes, the conductive material of the anode above the reservoir oxidizes and dissolves into solution, exposing the release system containing the molecules to be delivered to the surrounding fluids. The molecules to be delivered are released into the surrounding fluids by diffusion out of or by degradation of the release system. The frequency of release is controlled by incorporation of a miniaturized power source and microprocessor onto the microchip. Activation of any reservoir can be achieved by preprogramming the microprocessor, by remote control, or by a signal from a biosensor.

DESCRIPTION OF THE DRAWINGS

FIGS. 7a–c are schematic views of several configurations of active delivery devices.

DETAILED DESCRIPTION

Figure 1:
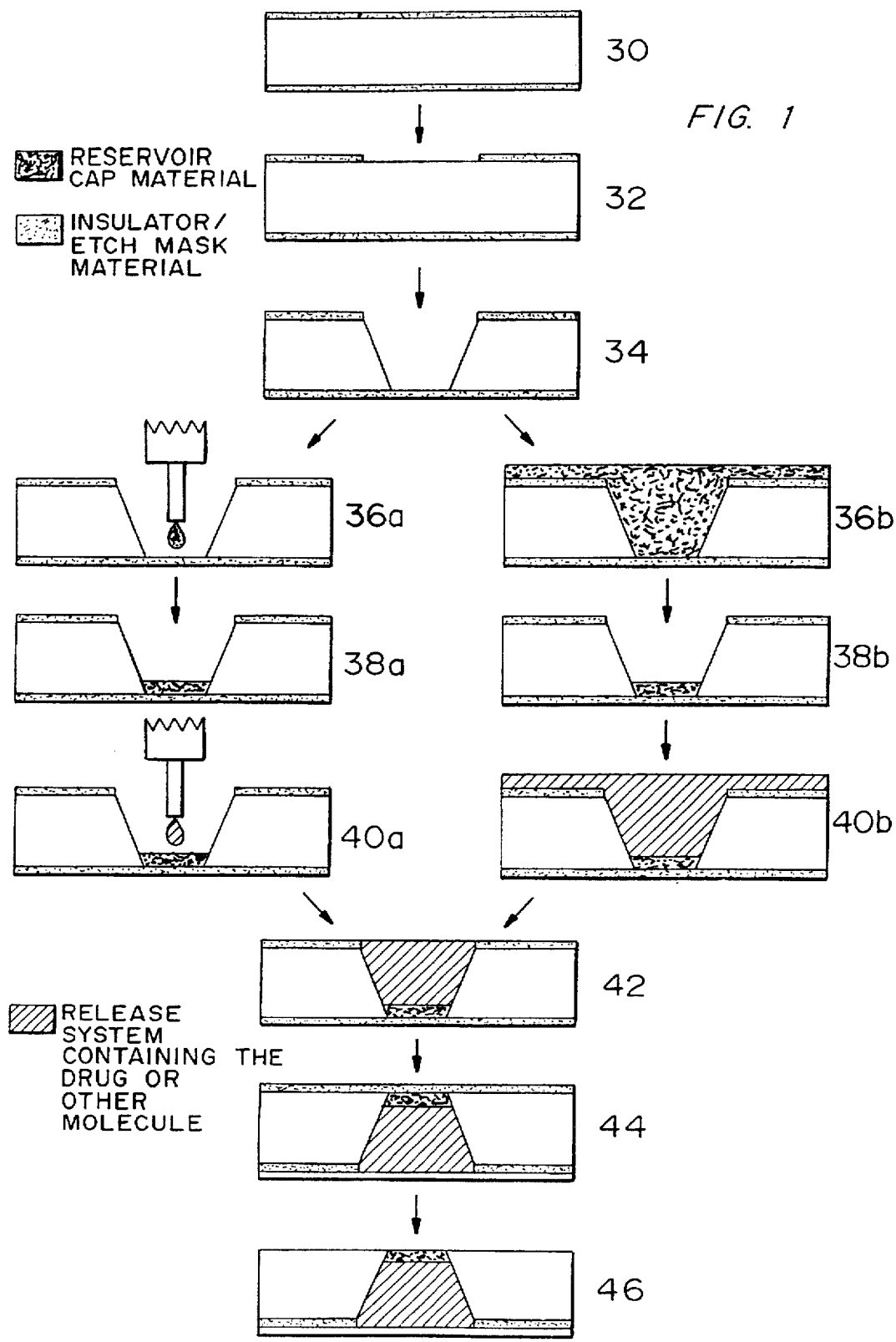
FIG. 1 depicts a typical fabrication scheme for a passive delivery device.

Microchip devices have been provided which can accurately deliver drugs and other molecules at defined rates and times according to the needs of the patient or other experimental system. As used herein, a "microchip" is a miniaturized device fabricated using methods commonly applied to the manufacture of integrated circuits such as ultraviolet (UV) photolithography, reactive ion etching, and electron beam evaporation, as described, for example, by S. Wolf and R. N. Tauber, *Silicon Processing for the VLSI Era, Volume 1-Process Technology*, Lattice Press, Sunset Beach, Calif., 1986; and R. C. Jaeger, *Introduction to Microelectronic Fabrication*, Volume V in the Modular Series on Solid State Devices, Addison-Wesley, Reading, Mass., 1988. The microchips provide control over the rate the molecules are released as well as the time at which release begins. The time of release can be controlled passively or actively. The microchip fabrication procedure allows the manufacture of devices with primary dimensions (length of a side if square or rectangular, or diameter if circular) ranging from a few millimeters to several centimeters. A typical device thickness is 300 μm. However, the thickness of the device can vary from approximately 10 μm to several millimeters. Changing the device thickness affects the maximum number of reservoirs that may be incorporated onto a microchip and the volume of each reservoir. In vivo applications of the device would typically require devices having a primary dimension of 2 cm or smaller. Devices for in vivo applications are small enough to be implanted using minimally invasive procedures. Smaller in vivo devices (on the order of a millimeter) can be implanted using a catheter or other injectable means. Devices for in vitro applications have fewer size restrictions and, if necessary, can be made much larger than the dimension ranges for in vivo devices.

Materials For Device Fabrication

Each device consists of a substrate, reservoirs, and a release system containing or enclosing the molecules to be delivered. Devices which control the release time of the molecules may include reservoir caps. Active devices may include control circuitry and a power source.

The substrate

The substrate contains the etched reservoirs and serves as the support for the microchip. Any material which can serve as a support, is suitable for etching, and is impermeable to the molecules to be delivered and to the surrounding fluids, for example, water, blood, electrolytes or other solutions, may be used as a substrate. Biocompatibility of the substrate material is preferred, but not required. For in vivo applications, non-biocompatible materials may be encapsulated in a biocompatible material, such as poly(ethylene glycol) or polytetrafluoroethylene-like materials, before use. One example of a strong, non-degradable, easily etched substrate that is impermeable to the molecules to be delivered and the surrounding fluids is silicon. In another embodiment, the substrate is made of a strong material that degrades over a period of time into biocompatible components. This embodiment is preferred for in vivo applications where the device is implanted and physical removal of the device at a later time is not feasible or recommended, for example, brain implants. An example of a class of strong, biocompatible materials are the poly(anhydride-co-imides), discussed by K. E. Uhrich et al., "Synthesis and characterization of degradable poly(anhydride-co-imides)", *Macromolecules*, 1995, 28, 2184–93.

Release system

The molecules to be delivered may be inserted into the reservoirs in their pure form, as a liquid solution or gel, or they may be encapsulated within or by a release system. As used herein, "release system" includes both the situation where the molecules are in pure form, as either a solid or liquid, or are in a matrix formed of biodegradable material or a material which releases incorporated molecules by diffusion or disintegration of the matrix. The molecules can be sometimes contained in a release system because the degradation or diffusion properties of the release system provide a method for controlling the release rate of the molecules. The molecules can be homogeneously or heterogeneously distributed within the release system. Selection of the release system is dependent on the desired rate of release of the molecules. Both non-degradable and degradable release systems can be used for delivery of molecules. Suitable release systems include polymers and polymeric matrices, non-polymeric matrices, or inorganic and organic excipients and diluents such as, but not limited to, calcium carbonate and sugar. Release systems may be natural or synthetic, although synthetic release systems are preferred due to the better characterization of release profiles. The release system is selected based on the period over which release is desired, generally in the range of at least three to twelve months for in vivo applications. In contrast, release times as short as a few seconds may be desirable for some in vitro applications. In some cases, continuous (constant) release from a reservoir may be most useful. In other cases, a pulse (bulk) release from a reservoir may provide more effective results. Note that a single pulse from one reservoir can be transformed into pulsatile release by using multiple reservoirs. It is also possible to incorporate several layers of a release system and other materials into a single reservoir to achieve pulsatile delivery from a single reservoir.

The release system material can be selected so that molecules of various molecular weights are released from a reservoir by diffusion through or degradation of the material. Biodegradable polymers, bioerodible hydrogels, and protein delivery systems are preferred for release of molecules by diffusion or degradation. In general, these materials degrade either by enzymatic hydrolysis or exposure to water in vivo or in vitro, or by surface or bulk erosion. Representative synthetic, biodegradable polymers include: poly(amides) such as poly(amino acids) and poly(peptides); poly(esters) such as poly(lactic acid), poly(glycolic acid), poly(lactic-co-glycolic acid), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), copolymers and mixtures thereof.

Representative synthetic, non-degradable polymers include: poly(ethers) such as poly(ethylene oxide), poly (ethylene glycol), and poly(tetramethylene oxide); vinyl polymers-poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; poly(siloxanes); and any chemical derivatives thereof (substitutions, additions of chemical groups, for example, alkyl, alkylene, hydroxylations, oxidations, and other modifications routinely made by those skilled in the art), copolymers and mixtures thereof.

Molecules to be released

Any natural or synthetic, organic or inorganic molecule or mixture thereof can be delivered. In one embodiment, the microchip is used to deliver drugs systemically to a patient in need thereof. In another embodiment, the construction and placement of the microchip in a patient enables the localized release of drugs that may be too potent for systemic delivery. As used herein, drugs are organic or inorganic molecules, including proteins, nucleic acids, polysaccharides and synthetic organic molecules, having a bioactive effect, for example, anaesthetics, vaccines, chemotherapeutic agents, hormones, metabolites, sugars, immunomodulators, antioxidants, ion channel regulators, and antibiotics. The drugs can be in the form of a single drug or drug mixtures and can include pharmaceutically acceptable carriers. In another embodiment, molecules are released in vitro in any system where the controlled release of a small (milligram to nanogram) amount of one or more molecules is required, for example, in the fields of analytic chemistry or medical diagnostics. Molecules can be effective as pH buffering agents, diagnostic agents, and reagents in complex reactions such as the polymerase chain reaction or other nucleic acid amplification procedures.

Reservoir caps

In the passive timed release drug delivery devices, the reservoir caps are formed from a material that degrades over time, or does not degrade but is permeable to the molecules to be delivered. These materials are preferably polymeric materials. Materials can be selected for use as reservoir caps to give a variety of degradation rates or permeabilities to enable the release of molecules from different reservoirs at different times and, in some cases, different rates. To obtain different release times (amounts of release time delay), caps can be formed of different polymers, the same polymer with different degrees of crosslinking, or a UV polymerizable polymer. In the latter case, varying the exposure of this polymer to UV light results in varying degrees of crosslinking and gives the cap material different diffusion properties or degradation rates. Another way to obtain different release times is by using one polymer, but varying the thickness of that polymer. Thicker films of some polymers result in delayed release time. Any combination of polymer, degree of crosslinking, or polymer thickness can be modified to obtain a specific release time or rate. In one embodiment, the release system containing the molecules to be delivered is covered by a degradable cap material which is nearly impermeable to the molecules. The time of release of the molecules from the reservoir will be limited by the time necessary for the cap material to degrade. In another embodiment, the cap material is non-degradable and is permeable to the molecules to be delivered. The physical properties of the material used, its degree of crosslinking, and its thickness will determine the time necessary for the molecules to diffuse through the cap material. If diffusion out of the release system is limiting, the cap material delays release. If diffusion through the cap material is limiting, the cap material determines the release rate of the molecules in addition to delaying release time.

In the active timed release devices, the reservoir caps consist of thin films of conductive material patterned in the shape of anodes surrounded by cathodes. Any conductive material that can oxidize and dissolve in solution upon application of an electric potential can be used for the fabrication of the anodes and cathodes. Examples of such materials include metals such as copper, gold, silver, and zinc, and some polymers, as described, for example, by I. C. Kwon et al., "Electrically erodible polymer gel for controlled release of drugs", Nature, 1991, 354, 291–93; and Y. H. Bae et al., "Pulsatile drug release by electric stimulus", ACS Symposium Series, 1994, 545, 98–110. The anode is defined as the electrode where oxidation occurs. The portion of the anode directly above the reservoir oxidizes and dissolves into solution upon the application of a potential between the cathode and anode. This exposes the release system to the surrounding fluids and results in the release of the molecules.

Device packaging, control circuitry, and power source

Microelectronic device packages are typically made of an insulating material such as aluminum oxide or silicon nitride. Their purpose is to allow all components of the device to be placed in close proximity and to facilitate the interconnection of components to power sources and to each other. For in vivo applications of the delivery device, the entire package, including all components (i.e. the device, the microprocessor, and the power source), are coated or encapsulated in a biocompatible material such as poly(ethylene glycol) or polytetrafluoroethylene-like materials. The materials requirements for in vitro applications may be less stringent and depend on the particular situation.

The control circuitry consists of a timer, a demultiplexer, a microprocessor, and a input source, for example, a memory source, a signal receiver, or a biosensor. The timer and demultiplexer circuitry can be designed and incorporated directly onto the surface of the microchip during electrode fabrication. The criteria for selection of a microprocessor are small size, low power requirement, and the ability to translate the output from memory sources, signal receivers, or biosensors into an address for the direction of power through the demultiplexer to a specific reservoir on the delivery device. Selection of a source of input to the microprocessor such as memory sources, signal receivers, or biosensors depends on the delivery device's particular application and whether device operation is preprogrammed, controlled by remote means, or controlled by feedback from its environment (i.e. biofeedback).

The criteria for selection of a power source are small size, sufficient power capacity, ability to be integrated into the control circuitry, the ability to be recharged, and the length of time before recharging is necessary. Several lithium-based, rechargeable microbatteries have been described by S. D. Jones and J. R. Akridge, "Development and performance of a rechargeable thin-film solid-state microbattery", Journal of Power Sources, 1995, 54, 63–67; and J. B. Bates et al., "New amorphous thin-film lithium electrolyte and rechargeable microbattery", IEEE 35$^{th}$ International Power Sources Symposium, 1992, 337–39. These batteries are typically only ten microns thick and occupy 1 cm$^2$ of area. One or more of these batteries can be incorporated directly onto the delivery device.

Methods of Device Fabrication

Fabrication of the reservoirs

Devices are manufactured using methods known to those skilled in the art, reviewed, for example, by Wolf et al. (1986); Jaeger (1988); Kwon et al. (1991); and Bae et al. (1994).

Figure 2:
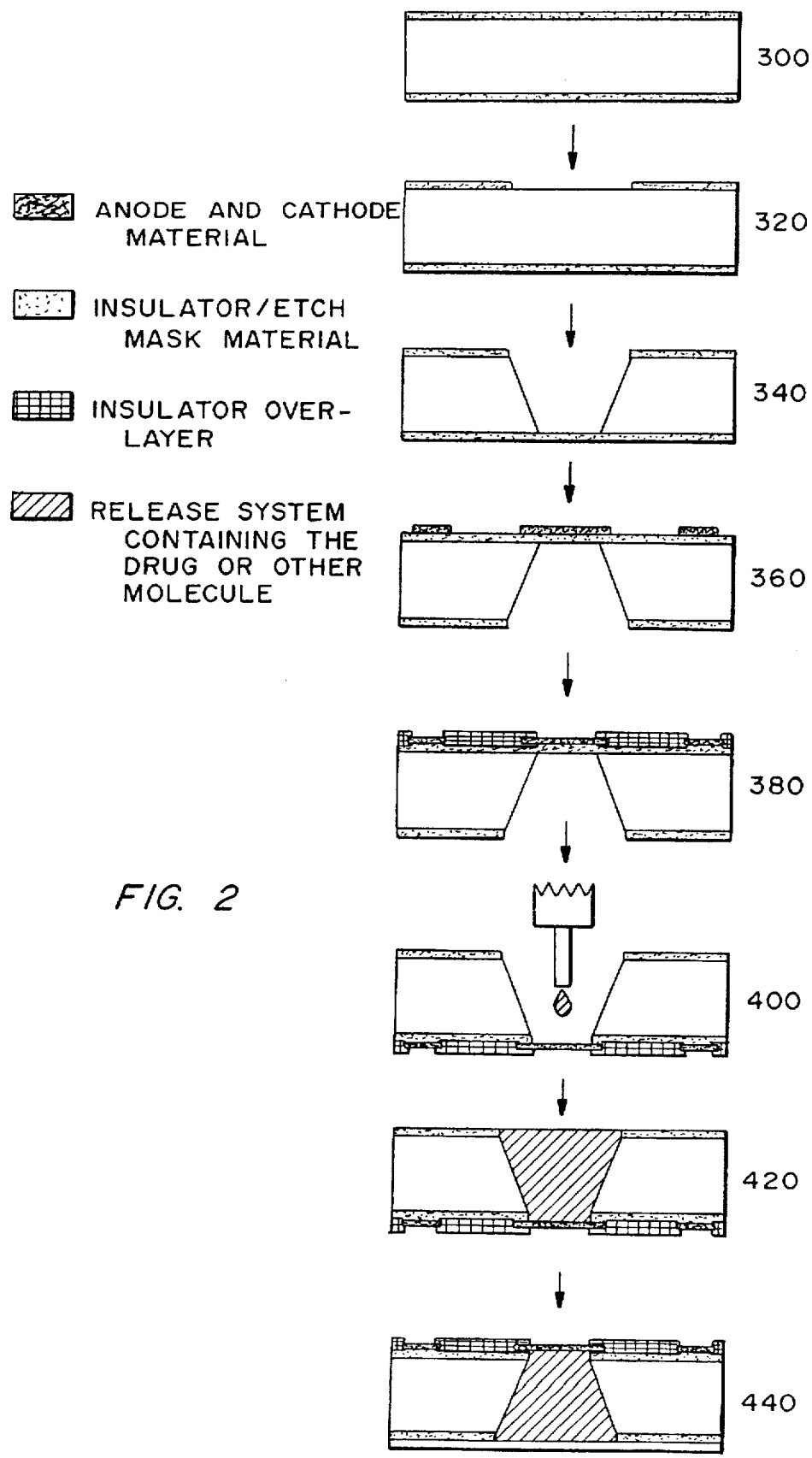
FIG. 2 depicts a typical fabrication scheme for an active delivery device.

In a preferred method of microchip manufacture, depicted in FIGS. 1 and 2, passive and active devices, respectively, fabrication begins by depositing and photolithographically patterning a material, typically an insulating material, onto the substrate to serve as an etch mask during reservoir etching. Typical insulating materials for use as a mask include silicon nitride, silicon dioxide, and some polymers. In a preferred embodiment, a thin film (approximately 3000–5000 Å) of amorphous silicon nitride ($SiN_x$) is deposited on both sides of a silicon wafer 30/300 by Plasma Enhanced Chemical Vapor Deposition (PECVD). Reservoirs are patterned into the silicon nitride film on one side of the wafer 32/320 by ultraviolet photolithography and chemical etching with a hydrofluoric acid solution. The patterned silicon nitride serves as an etch mask for the chemical etching of the exposed silicon 34/340 by a concentrated potassium hydroxide solution (approximately 38.5% wt. at a temperature of 80°–85° C.). Alternatively, the reservoirs can be etched into the substrate by dry etching techniques such as reactive ion etching or ion beam etching. These techniques are commonly used in the fabrication of microelectronic devices, as reviewed, for example, by Wolf et al. (1986) and Jaeger (1988). Use of these microfabrication techniques allows the incorporation of hundreds to thousands of reservoirs on a single microchip. In a passive device, the reservoirs may be as little as 2–3 µm apart. In an active device, the distance between the reservoirs may be slightly larger (approximately 10–15 µm) due to the space occupied by the electrodes surrounding the reservoirs. Reservoirs can be made in nearly any shape and depth, and need not pass completely through the substrate. In a preferred embodiment, the reservoirs etched into a (100) silicon substrate by potassium hydroxide are in the shape of a square pyramid having side walls sloped at 54° and pass completely through the substrate (approximately 300 µm) to the silicon nitride film on the other side of the substrate. (Here, the silicon nitride film serves as a potassium hydroxide etch stop.) The pyramidal shape allows easy filling of the reservoirs through the large opening of the reservoir (approximately 500 µm by 500 µm) on the patterned side of the substrate, release through the small opening of the reservoir (approximately 30 µm by 30 µm) on the other side of the substrate, and provides a large cavity inside the device for storing the drugs or other molecules to be delivered.

Fabrication of passive timed release reservoir caps

In the fabrication of passive timed release microchips, the reservoir cap material is injected with a micro-syringe 36a or spin coated 36b into a reservoir having the thin film of insulating mask material still present over the small opening of the reservoir. If injection is used, cap formation is complete after the material is injected into the reservoir 38a and does not require further processing. If spin coating is used, the cap material is planarized by multiple spin coatings 36b. The surface of the film is then etched by a plasma or an ion beam until the desired cap thickness is obtained 38b. In a preferred embodiment, the insulating material used is silicon nitride and the cap material is injected into the reservoir with a syringe.

Reservoir caps control the time at which molecules are released from the reservoirs. Each reservoir cap can be of a different thickness or have different physical properties to vary the time at which each release system containing the molecules is exposed to the surrounding fluids. Injection is the preferred method of filling deep (greater than 10 µm) reservoirs or reservoirs with large openings (greater than 100 µm). For example, to obtain different cap thicknesses using injection, different amounts of cap material are injected directly into each individual reservoir. Spin coating is the preferred method of filling shallow (less than 10 µm) reservoirs, reservoirs that do not pass completely through the substrate, or reservoirs with small (less than 100 µm) openings. Variation in cap thickness or material by spin coating can be achieved by a repeated, step-wise process of spin coating, masking selected reservoirs, and etching. For example, to vary cap thickness with spin coating, the cap material is spin coated over the entire substrate. Spin coating is repeated, if necessary, until the material is nearly planarized. A mask material such as photoresist is patterned to cover the cap material in all the reservoirs except one. Plasma or ion beam techniques are used to etch the cap material in the exposed reservoir to the desired thickness. The photoresist is then removed from the substrate. The process is repeated as a new layer of photoresist is deposited and patterned to cover the cap material in all the reservoirs except one (the exposed reservoir is not the same one already etched to its desired thickness). Etching of the exposed cap material in this reservoir continues until the desired cap thickness is obtained. This process of depositing and patterning a mask material such as photoresist, etching, and mask removal can be repeated until each reservoir has its own unique cap thickness. The techniques, UV photolithography, plasma or ion beam etching, etc., are well known to those skilled in the field of microfabrication.

Although injection and spin coating are the preferred methods of cap fabrication, it is understood that each reservoir can be capped individually by capillary action, by pulling the material into the reservoir using a vacuum or other pressure gradient, by melting the material into the reservoir, by centrifugation and related processes, by manually packing solids into the reservoir, or by any combination of these or similar reservoir filling techniques.

Once a cap fabrication method is selected, additional methods for controlling the time of release of molecules from a reservoir can be utilized. Two non-limiting examples include either UV polymerizable polymers or the layering of release system and cap materials. First, if the reservoir caps are made of either an injected or spin coated UV polymerizable polymer, each cap can be exposed to a different intensity of UV light to give varying degrees of crosslinking and therefore, different degradation rates for degradable caps or different permeabilities to the molecules for non-degradable caps. Second, layers of cap material, both degradable and non-degradable, can be inserted between layers of the release system containing the molecules to be delivered by injection, spin coating, or selective crosslinking. These and other similar methods allow complex release profiles (i.e. pulsatile delivery at irregular time intervals) to be achieved from a single reservoir.

If desired, a passive timed release device can be fabricated without reservoir caps. The rate of release of the molecules is thus solely controlled by the properties of the release system containing the molecule to be delivered.

Fabrication of active timed release reservoir caps

In a preferred embodiment, photoresist is patterned in the form of electrodes on the surface of the substrate having the reservoirs covered by the thin film of insulating material. The photoresist pattern is positioned such that the anode is directly over the covered opening of the reservoir. A thin film of conductive material having the ability to dissolve into solution upon application of an electric potential is deposited over the entire surface using deposition techniques such as chemical vapor deposition, evaporation, sputtering, spin coating, and other techniques known in the art. Exemplary materials include metals such as copper, gold, silver, and zinc and some polymers, as disclosed by Kwon et al.

(1991) and Bae et al. (1994). After film deposition, the photoresist is stripped from the substrate. This removes the deposited film, except in those areas not covered by photoresist (lift-off technique). This leaves conducting material on the surface of the substrate in the form of electrodes 360. The film thickness of the conductive material may range from 0.05 to several microns. The conductive film is patterned into electrodes using a mask and either wet or dry etching techniques. The anode serves as the reservoir cap and the cathode surrounds each anode. The process of patterning, depositing, and lift-off is repeated again to completely cover the electrodes, except for the region of the anode directly over the reservoir and the cathode surrounding the exposed anode 380. This material used to cover much of each electrode is usually an insulator such as silicon oxide ($SiO_x$) or silicon nitride ($SiN_x$). The purpose of this film is to protect the electrodes from corrosion in all areas where corrosion is not necessary for release.

The electrodes are positioned in such a way that when an electric potential is applied across the electrodes, the unprotected portion of the anode reservoir cap oxidizes and dissolves into solution, exposing the release system containing the molecules to the surrounding fluids. The molecules are released from the reservoir at a rate dependent upon the degradation rate of a degradable release system or the rate of diffusion of the molecules out of a non-degradable release system.

Removal of the insulator film (reservoir etch stop)

The thin film of insulating material covering the reservoir used as a mask and an etch stop during reservoir fabrication must be removed from the active timed release device before filling reservoir 400 and from the passive timed release device (if the reservoir extends completely through the substrate) after filling reservoir 44. The film may be removed in two ways. First, the film can be removed by an ion beam or reactive ion plasma. In a preferred embodiment, the silicon nitride film used as the insulating material can be removed by a reactive ion plasma composed of oxygen and tetrafluoromethane gases. Second, the film can be removed by chemical etching. For example, hydrofluoric acid can be used to etch silicon dioxide.

Reservoir filling

The release system containing the molecules for delivery is inserted into the large opening of the reservoir by injection or spin coating 40a/40b/400. Each reservoir can contain a different molecule and dosage. Similarly, the release kinetics of the molecule in each reservoir can be varied by the choice of the release system and cap materials. In addition, the mixing or layering of release system and cap materials in each reservoir can be used to tailor the release kinetics to the needs of a particular application.

The distribution over the microchip of reservoirs filled with the release system containing the molecules to be delivered can vary depending on the medical needs of the patient or other requirements of the system. For applications in drug delivery, for example, the drugs in each of the rows can differ from each other. One row may contain a hormone and another row may contain a metabolite. Also, the release system can differ within each row to release a drug at a high rate from one reservoir and a slow rate from another reservoir. The dosages can also vary within each row. For those devices having deep (greater than 10 μm) reservoirs or reservoirs with large (larger than 100 μm) openings, differences in reservoir loading can be achieved by injection of different amounts of material directly into each reservoir. Variation between reservoirs is achieved in devices having shallow (less than 10 μm) reservoirs, reservoirs that do not pass completely through the substrate, or reservoirs with small (less than 100 μm) openings by a repeated, step-wise process of masking selected reservoirs, spin coating, and etching, as described above regarding the fabrication by spin coating of passive timed release reservoir caps. Preferably, the release system and molecules to be delivered are mixed before application to the reservoirs. Although injection and spin coating are the preferred methods of filling reservoirs, it is understood that each reservoir can be filled individually by capillary action, by pulling the material into the reservoir using a vacuum or other pressure gradient, by melting the material into the reservoir, by centrifugation and related processes, by manually packing solids into the reservoir, or by any combination of these or similar reservoir filling techniques.

Device packaging, control circuitry, and power source

The openings through which the reservoirs of passive and active devices are filled are sealed with a waterproof epoxy or other appropriate material impervious to the surrounding fluids 44/440. For in vitro applications, the entire unit, except for the face of the device containing the reservoirs and electrodes, is encased in a material appropriate for the system. For in vivo applications, the unit would be encapsulated in a biocompatible material such as poly(ethylene glycol) or polytetrafluoroethylene.

Figure 3:
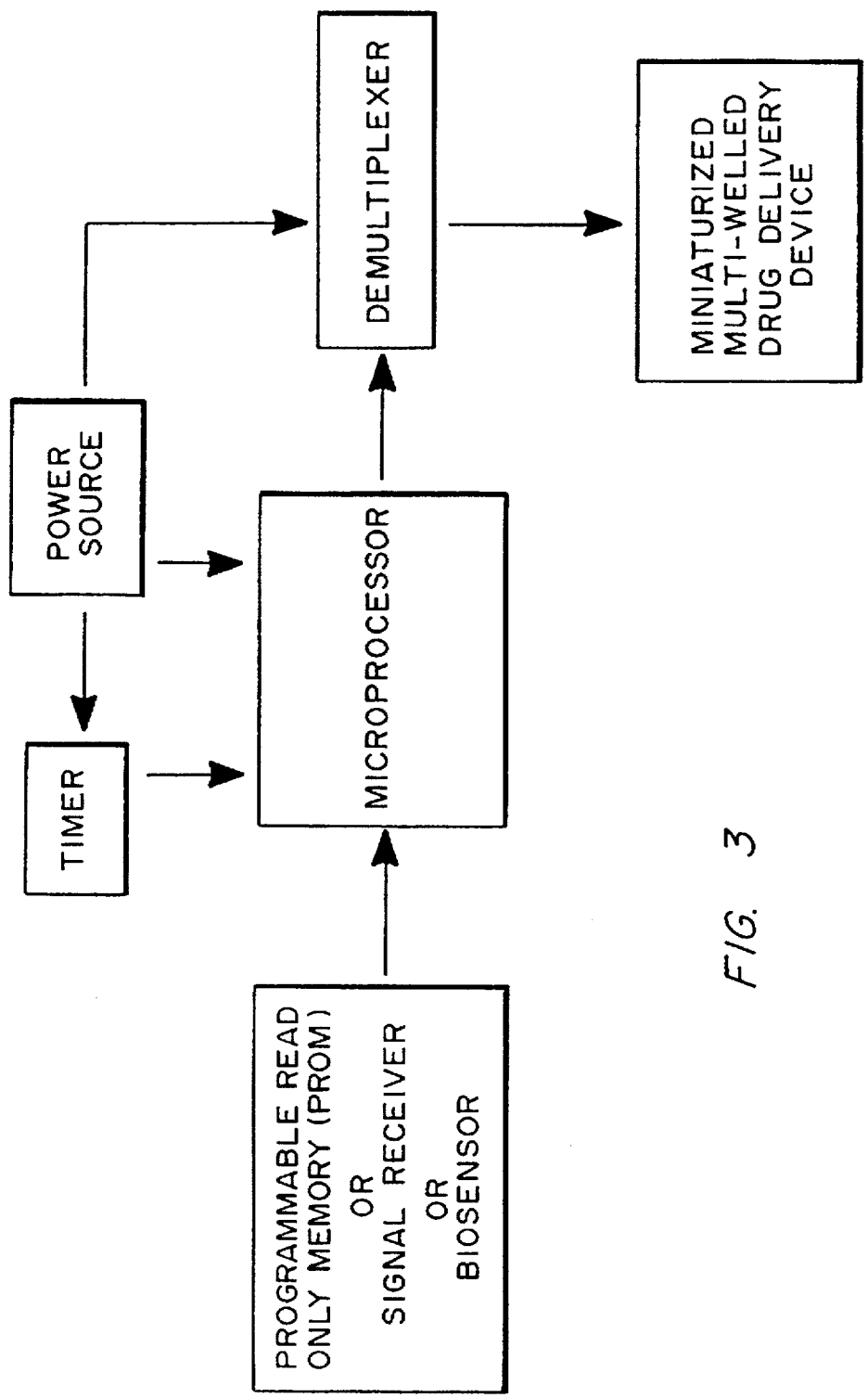
FIG. 3 depicts a typical device control circuitry flowsheet.

The mechanism for release of molecules by the active timed release device does not depend on multiple parts fitted or glued together which must retract or dislodge. Control of the time of release of each reservoir can be achieved by a preprogrammed microprocessor, by remote control, by a signal from a biosensor, or by any combination of these methods, as shown schematically in FIG. 3. First, a microprocessor is used in conjunction with a source of memory such as programmable read only memory (PROM), a timer, a demultiplexer, and a power source such as a microbattery, such as is described, for example, by Jones et al. (1995) and Bates et al. (1992). The release pattern is written directly into the PROM by the user. The PROM sends these instructions to the microprocessor. When the time for release has been reached as indicated by the timer, the microprocessor sends a signal corresponding to the address (location) of a particular reservoir to the demultiplexer. The demultiplexer sends an input, such as an electric potential, to the reservoir addressed by the microprocessor. A microbattery provides the power to operate the PROM, timer, and microprocessor, and provides the electric potential input that is directed to a particular reservoir by the demultiplexer. The manufacture, size, and location of each of these components is dependent upon the requirements of a particular application. In a preferred embodiment, the memory, timer, microprocessor, and demultiplexer circuitry is integrated directly onto the surface of the chip. The microbattery is attached to the other side of the chip and is connected to the device circuitry by vias or thin wires. However, in some cases, it is possible to use separate, prefabricated, component chips for memory, timing, processing, and demultiplexing. These are attached to the backside of the miniaturized delivery device with the battery. The size and type of prefabricated chips used depends on the overall dimensions of the delivery device and the number of reservoirs. Second, activation of a particular reservoir by the application of an electric potential can be controlled externally by remote control. Much of the circuitry used for remote control is the same as that used in the preprogrammed method. The main difference is that the PROM is replaced by a signal receiver. A signal such as radio waves, low power laser, or ultrasound is sent to the receiver by an external source, for example, computers or ultrasound generators. The signal is sent to the microprocessor where it is translated into a reservoir address. Power is then directed through the demultiplexer to the reservoir having the appropriate address. Third, a biosensor is integrated into the microchip to detect molecules in the surrounding fluids. When the concentration of the molecules reaches a certain level, the sensor sends a signal to the microprocessor to activate one or more reservoirs. The microprocessor directs power through the demultiplexer to the particular reservoir(s).

Microchip Applications

Passive and active microchip devices have numerous in vitro and in vivo applications. The microchip can be used in vitro to deliver small, controlled amounts of chemical reagents or other molecules to solutions or reaction mixtures at precisely controlled times and rates. Analytical chemistry and medical diagnostics are examples of fields where the microchip delivery device can be used. The microchip can be used in vivo as a drug delivery device. The microchips can be implanted into a patient, either by surgical techniques or by injection. The microchips provide delivery of drugs to animals or persons who are unable to remember or be ambulatory enough to take medication. The microchips further provide delivery of many different drugs at varying rates and at varying times of delivery.

The present invention will be further understood by reference to the following non-limiting examples Example 1: Microchip with Passive Timed Drug Release.

Figure 4:
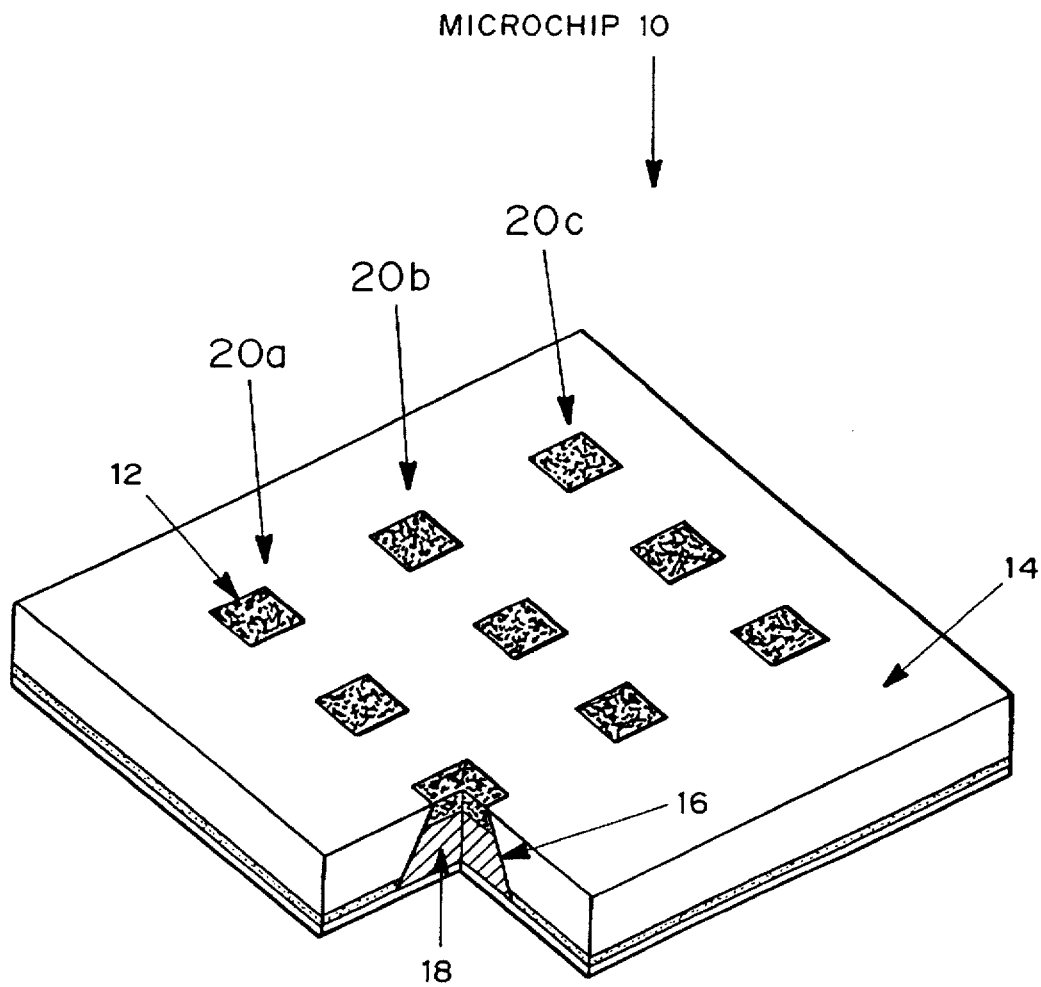
FIG. 4 depicts a passive delivery device.

A passive timed release device, microchip 10 is shown in FIG. 4. Microchip 10 is formed from substrate 14. Reservoirs 16 are etched into substrate 14. Positioned in reservoirs 16 is a release system containing molecules 18 for delivery. The reservoirs are capped with reservoir caps 12. The release system and the molecules for delivery 18 can vary between rows 20a, 20b, 20c, and within reservoirs of each row.

Microchip 10 can be inserted into solution for in vitro applications or be implanted in a selected part of the body for in vivo applications and left to operate without requiring further attention. When exposed to the surrounding fluids, reservoir caps 12 will degrade or become permeable to the release system containing molecules for delivery 18.

Example 2: Microchip with Active Controlled Time Release.

Figure 5:
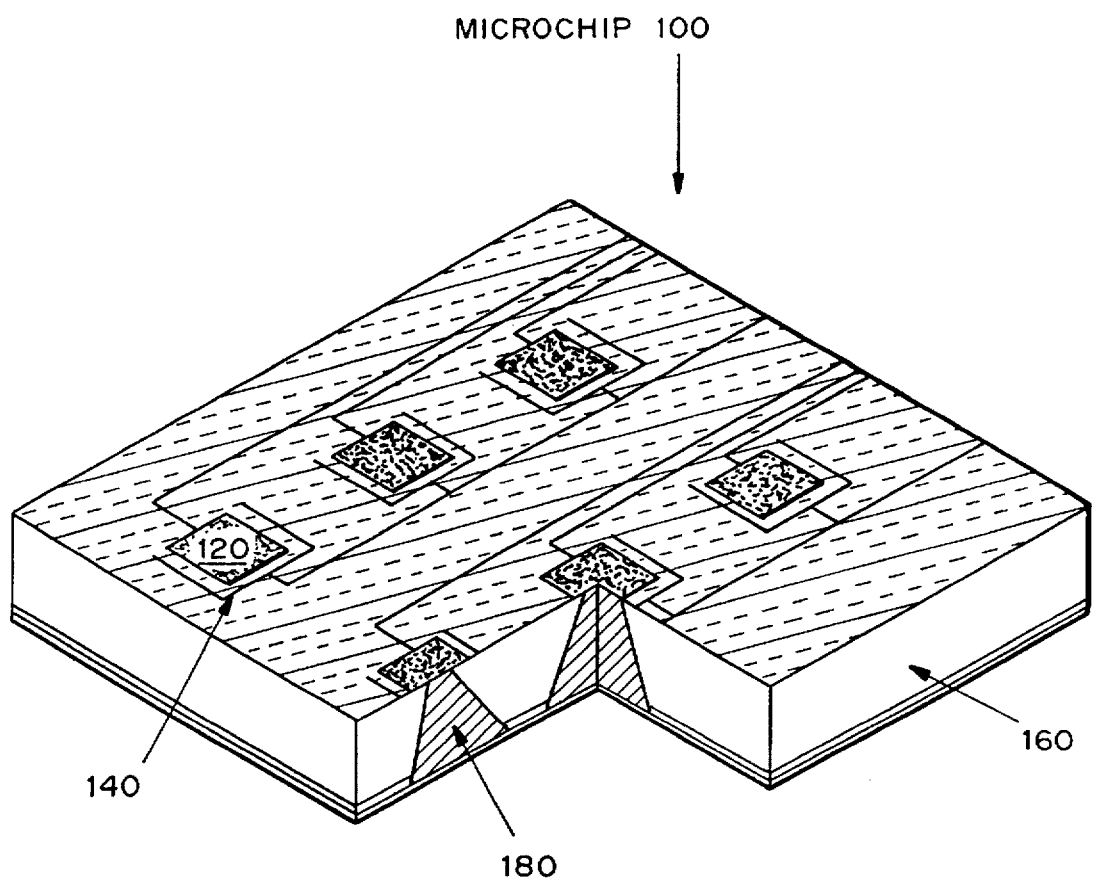
FIG. 5 depicts an active delivery device.
Figure 6A:
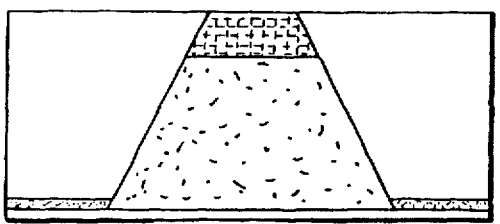
FIGS. 6a–i are schematic views of several configurations of passive delivery devices.
Figure 6E:
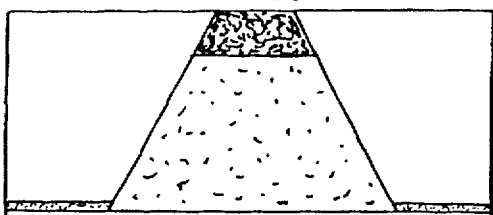
Figure 6B:
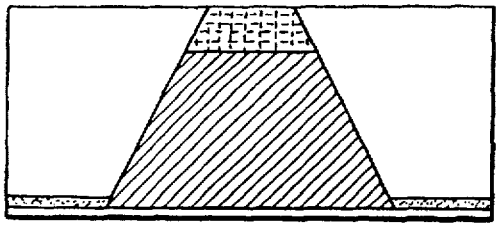
Figure 6F:
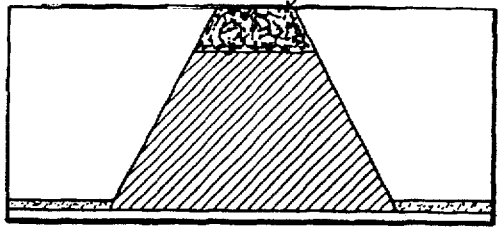
Figure 6C:
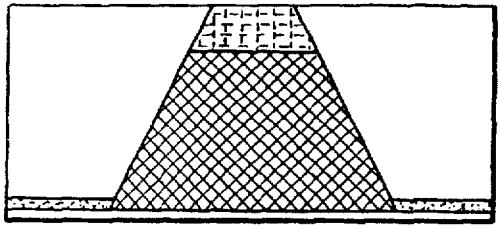
Figure 6G:
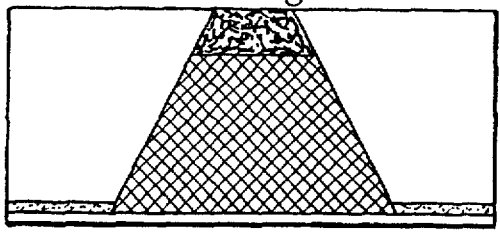
Figure 6D:
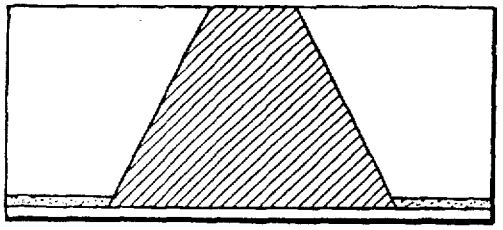
Figure 6H:
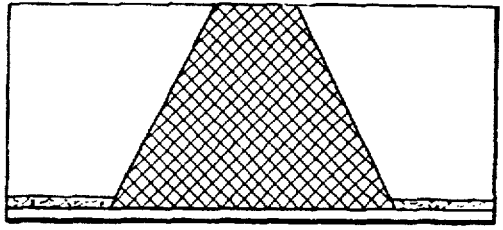
Figure 6I:
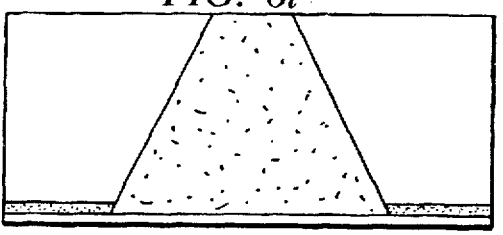

A drug delivery device that provides active timed release is shown as microchip 100 in FIG. 5. Microchip 100 is similar to microchip 10 except that microchip 100 contains electrodes that provide for active timed release. Microchip 100 is formed from substrate 160, release system containing molecules 180 for delivery, anode reservoir caps 120, and cathodes 140. Preferably, microchip 100 further includes an input source, a microprocessor, a timer, a demultiplexer, and a power source (not shown). The power source provides energy to drive the reaction between selected anodes and cathodes. Upon application of a small potential between the electrodes, electrons pass from the anode to the cathode through the external circuit causing the anode material to oxidize and dissolve into the surrounding fluids, exposing the release system containing the molecules for delivery 180 to the surrounding fluids. The microprocessor directs power to specific electrode pairs through a demultiplexer as directed by a PROM, remote control, or biosensor.

One skilled in the art would understand that the foregoing examples do not illustrate all of the variations which are included within the scope of the claimed miniaturized, multi-welled delivery device.

We claim:

1. A microchip device for the release of molecules comprising
a substrate,
at least two reservoirs in the substrate containing the molecules, and
each reservoir having a reservoir cap positioned on the reservoir over the molecules so that the molecules are released from the device by diffusion through or upon disintegration of the reservoir caps, and
wherein release of the molecules from the reservoir is controlled by said diffusion through or disintegration of the reservoir cap.

2. The device of claim 1 further comprising a plurality of reservoirs comprising different types of molecules, different amounts of molecules, or combinations thereof.

3. The device of claim 1 wherein release of the molecules is controlled by a release system incorporating the molecules in the reservoir.

4. The device of claim 3 wherein at least one reservoir cap is disintegratable and the release system in a reservoir is disintegratable to release the molecules after the disintegration of the reservoir cap.

5. The device of claim 3 wherein the reservoir comprises layers of different release system and reservoir cap materials such that pulsatile release is obtained.

6. The device of claim 3 wherein at least one reservoir cap is disintegratable and the release system is non-disintegratable, and diffusion of the molecules out of the release system provides a pulsed release of the molecules after the disintegration of the reservoir cap.

7. The device of claim 3 further comprising a cathode, a microprocessor, a timer, a demultiplexer, and a power source, wherein at least one reservoir cap is an anode, wherein upon application of an electric potential between the cathode and anode, at least one reservoir cap disintegrates, and exposes the underlying release system to the surrounding fluids.

8. The device of claim 7 wherein each reservoir is capped by an anodic reservoir cap, wherein the microprocessor function is directed by a source of memory preprogrammed to control the application of an electric potential between the cathode and the anode of individual reservoirs at specific times.

9. The device of claim 7 wherein the microprocessor function is directed by remote control to control the application of an electric potential between the cathode and the anode of the reservoir.

10. The device of claim 7 further comprising a biosensor, wherein the microprocessor function is directed by the biosensor to control the application of an electric potential between the cathode and the anode of the reservoir.

11. The device of claim 3 wherein the release system comprises drug molecules in an excipient or diluent.

12. The device of claim 3 wherein the release system in the reservoir is formed of the molecules to be released, wherein the dissolution rate of the molecules determines the rate of release of the molecules.

13. The device of claim 1 wherein at least one reservoir cap is disintegratable and wherein the disintergragtion rate of the cap determines the time at which the molecules are released from the reservoir.

14. The device of claim 13, further comprising a plurality of reservoirs and reservoir caps wherein the reservoir caps have different thicknesses.

15. The device of claim 1 wherein at least one reservoir cap is non-disintegratable and wherein the rate of diffusion of the molecules through the cap determines the time at which the molecules are released from the reservoirs.

16. A method for the delivery of molecules comprising providing at a site where the molecules are to be delivered a microchip device for the release of molecules, wherein the microchip comprises a substrate, at least two reservoirs in the substrate containing the molecules to be delivered, and each reservoir having a reservoir cap positioned on the reservoir so that the molecules are released from the device by diffusion through or upon disintegration of the reservoir caps, and controlling the release of the molecules from the reservoir by said diffusion through or disintegration of the reservoir cap.

17. The method of claim 16 wherein the molecules are drugs, comprising implanting or injecting the microchip into a patient.

18. The method of claim 17 wherein the molecules are a drug selected from the group consisting of nucleic acids, proteins, amino acids, polysaccharides, and organic or synthetic molecules.

19. The method of claim 18 wherein the drugs are in combination with a pharmaceutically acceptable carrier.

20. The method of claim 16 wherein the molecules are diagnostic or chemical reagents.

21. The method of claim 16 wherein the molecules are released in a pulsatile or continuous manner.

22. The method of claim 16 further comprising controlling the release of the molecules by a release system incorporating the molecules in the reservoir.

23. The method of claim 22 wherein the release system is formed by the molecules to be released.

24. The method of claim 22 wherein at least one reservoir cap is disintegratable and the reservoir caps are positioned on the reservoirs over the release system, wherein the disintegration rate of the cap or rate of molecule diffusion through the cap determines the time at which the molecules are released from the reservoir.

25. The method of claim 22 wherein the device further comprises a cathode, a microprocessor, a timer, a demultiplexer, and a power source, wherein at least one reservoir cap is an anode and wherein the method further comprises applying an electric potential between the cathode and anode, to oxidize the reservoir cap and expose the underlying release system to the surrounding fluids.

26. The method of claim 25 wherein the microprocessor function is directed by a source of memory preprogrammed to control the application of an electric potential between the cathode and the anode of individual reservoirs at specific times, wherein the method further comprises programming the memory.

27. The method of claim 25 wherein the method further comprises directing the microprocessor function by remote control to control the application of an electric potential between the cathode and the anode of each reservoir.

28. The method of claim 25 wherein the device further comprises a biosensor, wherein the method further comprises directing the microprocessor function by the biosensor to control the application of an electric potential between the cathode and the anode of each reservoir.

29. The method of claim 16 wherein at least one reservoir cap is non-disintegratable and wherein the rate of diffusion of the molecules through the cap determines the time at which the molecules are released from the reservoirs.

* * * * *

UNITED STATES PATENT AND TRADEMARK OFFICE
CERTIFICATE OF CORRECTION

PATENT NO. : 5,797,898
DATED : August 25, 1998
INVENTOR(S) : John T. Santini, Jr., et al It is certified that error appears in the above-identified patent and that said Letters Patent is hereby corrected as shown below:

On the title page, item [75], add the following: Achim Göpferich, Erlangen, Germany --

On the title page, item [56], under "OTHER PUBLICATIONS", first reference, delete "Rae" and insert --Bae--.

IN THE DRAWINGS

Delete Drawing Sheet 7 and substitute therefor the Drawing Sheet, consisting of FIGS. 7a, 7b, and 7c, as shown on the attached page.

Column 7, line 30, delete "(100)" and insert --(100)--.

UNITED STATES PATENT AND TRADEMARK OFFICE
CERTIFICATE OF CORRECTION

PATENT NO. : 5,797,898    PAGE 2 OF 3
DATED : August 25, 1998
INVENTOR(S) : John T. Santini, Jr., et al It is certified that error appears in the above-identified patent and that said Letters Patent is hereby corrected as shown below:

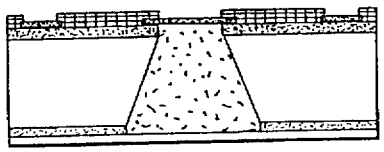

FIG. 7a

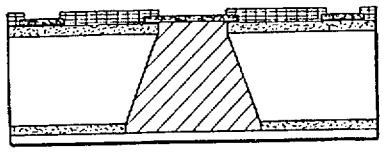

FIG. 7b

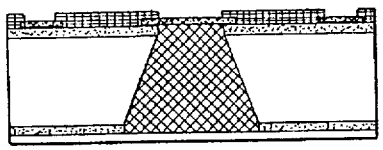

FIG. 7c

UNITED STATES PATENT AND TRADEMARK OFFICE
CERTIFICATE OF CORRECTION

PATENT NO. : 5,797,898  
DATED : August 25, 1998  
INVENTOR(S) : John T. Santini, Jr., et al It is certified that error appears in the above-identified patent and that said Letters Patent is hereby corrected as shown below:

 INSULATOR / ETCH MASK MATERIAL

 ANODE AND CATHODE MATERIAL

 INSULATOR OVERLAYER

 DEGRADABLE RELEASE SYSTEM

 NON-DEGRADABLE RELEASE SYSTEM

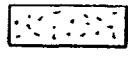 PURE DRUG OR OTHER MOLECULE (SOLID, LIQUID, OR GEL FORM)

Signed and Sealed this

Eighteenth Day of May, 1999

Attest:

Q. TODD DICKINSON

Attesting Officer     Acting Commissioner of Patents and Trademarks